United States Patent [19]
Lezdey et al.

[11] Patent Number: 5,217,951
[45] Date of Patent: * Jun. 8, 1993

[54] TREATMENT OF INFLAMMATION

[76] Inventors: John Lezdey, 976 Kingston Dr., Cherry Hill, N.J. 08034; Allan J. Wachter, 9822 S. Grandview, Tempe, Ariz. 85284

[*] Notice: The portion of the term of this patent subsequent to Nov. 24, 2009 has been disclaimed.

[21] Appl. No.: 781,003

[22] Filed: Oct. 18, 1991

Related U.S. Application Data

[63] Continuation-in-part of Ser. No. 643,727, Jan. 18, 1991, abandoned, which is a continuation-in-part of Ser. No. 598,241, Oct. 16, 1990, abandoned, and a continuation-in-part of Ser. No. 591,630, Oct. 2, 1990, Pat. No. 5,114,917, which is a continuation-in-part of Ser. No. 445,005, Dec. 4, 1989, Pat. No. 5,008,242, which is a continuation-in-part of Ser. No. 242,735, Sep. 9, 1988, abandoned, and a continuation-in-part of Ser. No. 181,707, Apr. 14, 1988, abandoned, Ser. No. 242,735, Apr. 14, 1988, and Ser. No. 181,707, Apr. 14, 1988, each is a continuation-in-part of Ser. No. 946,445, Dec. 24, 1986, abandoned.

[51] Int. Cl.$^5$ ............................................. A61K 37/64
[52] U.S. Cl. ......................................... 514/8; 514/2; 514/21; 530/395
[58] Field of Search ................... 514/2, 8, 21; 530/395

[56] References Cited

U.S. PATENT DOCUMENTS

| 4,916,117 | 4/1990 | Lezdey et al. | 514/8 |
| 5,008,242 | 4/1991 | Lezdey et al. | 514/8 |

OTHER PUBLICATIONS

Measurement of histamine-releasing factor activity in individual nasal washings: Relationship w/atopy, basophil response, and membrane-bound IgE. Sim et al, J. Allergy Clin. Immunol., Jun. 1992.
Insights In Allergy—vol. 5, No. 1—Apr. 1990.

Primary Examiner—Michael G. Wityshyn
Assistant Examiner—Choon Koh
Attorney, Agent, or Firm—John Lezdey

[57] ABSTRACT

A method for the prophylaxis or direct treatment of non-bronchial mast cell implicated diseases or injuries in a patient which comprises administering to the site of the disease or injury an effective amount of at least one serine protease inhibitor, its salts, derivatives or analogs which bind with the mast cells or their mediators.

12 Claims, No Drawings

TREATMENT OF INFLAMMATION

RELATED APPLICATION

This application is a continuation-in-part of application Ser. No. 643,727 filed Jan. 18, 1991, now abandoned, which is a continuation-in-part of application Ser. No. 598,241 filed Oct. 16, 1990, of Lezdey et al, now abandoned, and application Ser. No. 591,630 filed Oct. 2, 1990, now U.S. Pat. No. 5,114,917, which is a continuation-in-part of application Ser. No. 445,005 filed Dec. 4, 1989, now U.S. Pat. No. 5,008,242, which is a continuation-in-part of application Ser. No. 242,735 filed Sep. 9, 1988, now abandoned, and application Ser. No. 181,707 filed Apr. 14, 1988, now abandoned, which are continuations-in-part of application Ser. No. 946,445 filed Dec. 24, 1986, now abandoned.

FIELD OF THE INVENTION

The present invention relates to a method and composition for treating mammals afflicted with non-bronchial mast cell implicated disease. More particularly, the present invention relates to the treatment of certain mast cell implicated non-bronchial diseases, particularly inflammatory conditions in patients, by administering serine protease inhibitors, their analogs, salts or derivatives. There is particularly provided topical compositions for treating the symptoms of inflammatory skin conditions. The inhibitors bind with mast cell and/or T-cell mediators.

BACKGROUND OF THE INVENTION

Prior to the present invention it was generally believed that serine protease inhibitors could be used only to supplement a deficiency occurring as a result of a genetic defect or a chemically produced deficiency resulting from an event such as smoking. Moreover, no consideration was previously given for directly controlling diseases in which mast cells are implicated by administering serine protease inhibitors when serum levels of proteases or protease inhibitors are normal. Mast cells have been found to be implicated in diseases and events such as allergic and non-allergic rhinitis, nasal polyposis, atopic dermatitis, including psoriasis, contact dermatitis, pancreatitis, emphysema, asthma, colitis, Crohn's Disease, wound healing, cluster headaches, coronary artery spasm, etc.

The role of mast cells in humans is the same as in animals. In addition, animals contain counterparts to human α-1-antichymotrypsin, α-1-antitrypsin, and other serine protease inhibitors. In fact, it has been shown that human α-1-antitrypsin will bind with animal mast cells and the mediators derived therefrom.

Inflammation is a non-specific response of tissues to diverse stimuli or insults and results in release of a variety of materials at the site of inflammation that induce pain. It is now recognized that mast cells are implicated in the pathophysiology of inflammatory skin conditions as well as in other physiological disorders. Mast cells provide the greatest source of histamines in acute inflammation. Mast cells have also been noted in hypertropic scars.

Eosinophils, basophils and neutrophils are prominent in inflammatory lesions due to the potent chemoattractants released by mast cells.

Neutrophils are a main source of serine elastase and cathepsin G which are important in the tissue damage of inflammation.

The most direct approach to therapy of inflammatory skin conditions appears to be a direct attack at the site of inflammation of the mediators of inflammation and pain and the reduction of those neutrophilic derivatives which can cause damage to the growth of new tissue during the healing process.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Alpha 2-macroglobulin is a glycoprotein containing 8–11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha-1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Inhibitors. 1st, 1–21 (1970).

The article of Groutas entitled "Inhibitors of Leukocyte Elastase and Leukocyte Cathepsin G Agents for the Treatment of Emphysema and Related Ailments" medical Research Reviews, Vol. 7, No. 7, 227–241 (1987), discloses the role of eglin, elastinal 1 and elasnin in emphysema.

U.S. Pat. No. 4,916,117 to Lezdey et al discloses the treatment of pulmonary inflammation with microcrystalline alpha-1-antichymotrypsin.

It is understood that the term "serine protease inhibitors" as used herein refers to the inhibitors derived from a human source and the corresponding recombinant product which is either glycosylated or non-glycosylated.

SUMMARY OF THE INVENTION

The present invention relates to a method for treating non-bronchial inflammatory conditions in patients by the administration of serine protease inhibitors, their analogs, salts or derivatives which alone or in combination with one or more other serine protease inhibitors which have a specific activity for mast cells or the proteases derived therefrom such as cathepsin-G, elastase, human mast cell chymase, kinins or their precursors in a suitable pharmaceutical composition.

Serine protease inhibitors have been found to play a major role in the direct inactivation of the mediators of inflammation so that the normal wound healing process can be accelerated without interference from the excess of materials released at the site of inflammation. The almost immediate disappearance of pain and itch indicates that there can be a control of the kinins as well. A cocktail of serine protease inhibitors would therefore be useful to deactivate those mediators of inflammation which may not yet be recognized or are found in association with a particular disease.

As presently found, serine protease inhibitors are useful in the treatment of burn patients which not only experience pain and itch but have a problem in controlling the laydown of organized collagen because of elastase and cathepsin G; serine protease inhibitors permit the rapid growth of normal skin.

The administration of serine protease inhibitors appears to be a viable alternative to the administration of steroids to reduce inflammation and to treat inflammatory skin conditions not treatable with steroids or reduce the steriod requirement.

It has now been found that controlling the amount of the destructive enzymes at the site of inflammation can prevent proliferation of the disease, prevent associated tissue damage and promote healing. It has also been found that the administration of serine protease inhibitors which inactivate destructive proteases alone provide a major control of the symptoms of the disease or burns. However, since the cause of disease may be a result of more than one factors, the use of more than one protease inhibitor provides a better chance of success for early remission of the symptoms and for a prophylactic control of the symptoms associated with the disease. Serine protease inhibitors, for example, alpha 2-macroglobulin, alpha 1-antichymotrypsin and C-reactive protein (CRP), when administered to the site of inflammation provides a reduction in swelling, pain and stiffness.

For chronic cases of dermatitis, a cocktail of protease inhibitors is preferably administered at the site of inflammation. The treatment can be followed with the addition of an appropriate steroid or antibiotic.

The serine protease inhibitors which are contemplated in the present invention are any of the inhibitors, their analogs, derivatives or salts which can inhibit mast cells or bind with any one or more of the protease derived from eosinophils, basophils and/or neutrophils such as elastase, cathepsin-G, tryptase, chymase, kinins, kallikrein, tumor necrosis factor, chymotrypsin, collagenase, and the like.

The serine protease inhibitors included in the present invention are alpha 1-antichymotrypsin, alpha 1-antitrypsin, alpha 2-macroglobulin, alpha 2-antiplasmin, elastinal 1, elasnin 3, C-reactive protein, beta 1-antigellagenase, serine amyloid A protein, alpha cysteine protease inhibitors, inter-alpha-trypsin inhibitor, secretory leucocyte protease inhibitor, bronchial mucous inhibitor, and C-1-inhibitor. The inhibitors of the invention may be natural or prepared by recombinant means.

Alpha 2-antiplasmin is a single-chain glycoprotein containing 11% carbohydrate, and asparagine and leucine as the amino terminal residues. This enzyme has a molecular weight of about 65,000 to 70,000. This inhibitor can inactivate Kallikrein, chymotrypsin ($Kass = 1.0 \times 10^5$ $M^{-1}$ $sec^{-1}$), plasmin, Factor Xa and Factor XIa.

The use of alpha 1-antitrypsin and alpha 1-antichymotrypsin have been especially useful in the treatment of the various inflammatory skin conditions including those which are induced by autoimmune disease, virus and bacterial infections. The serine protease inhibitors have also been found to cause vasoconstriction, which in inflammation, decreases swelling and redness and to eliminate pain and itching. This feature is especially useful in burns and atopic dermatitis.

Alpha 1-antitrypsin has also been found especially useful in the treatment of topical inflammatory conditions because of its association with elastase. Alpha 1-antitrypsin inhibits glycosylation enhancing factor (GEF) from T-cells so as to prevent degranulation of masts cells by IgE. However, it is preferably used in combination with alpha 1-antichymotrypsin which binds with basophils to inhibit histamine release.

Both alpha 1-antitrypsin and alpha 1-antichymotrypsin alone or in combination control the release of histamines.

The drugs of the invention may be prepared by cloning, by conventional techniques utilizing an oligonucleotide probe or antibody probe, and the like. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

Some inflammation conditions are not immediately identifiable as to source and the factors which are involved to produce the different symptoms are not readily apparent. Therefore, it is desirable to administer in some case a combination or cocktail of serine protease inhibitors to provide a broad spectrum of drugs which can provide rapid relief of the different symptoms of inflammation. The most effective combination is alpha 1-antichymotrypsin and alpha 1-antitrypsin and/or alpha 2-macroglobulin. Preferably, the combination is administered in a ratio of 1:1:1: to 3:2:1: either in a single unit or in separate dosage form.

When topically applied, a serine protease inhibitor such as alpha 1-antitrypsin in suitable composition form is useful in the treatment of burns and inflammatory skin diseases such as psoriasis, eczema, acne, and the like. It has been demonstrated that treatment with alpha 1-antichymotrypsin together with $\alpha$1-antitrypsin has reduced pain when applied to skin lesions.

The use of a non-aqueous lipid miscible carrier, for example, such as prepared with liposomes are particularly advantageous since they provided improved activity at the treatment sites.

The compositions of the invention are preferably administered to patients showing an increase in IgE through a patch or serum test. That is, the patient shows a positive allergic condition.

It is therefore an object of the invention to provide an antiinflammatory composition which can relieve the swelling and redness associated with inflammatory conditions in humans and animals.

It is a further object of the invention to provide an antiinflammatory composition which is well tolerated by the human body and is free of side effects, and for its counterparts for animal use.

It is a yet still further object of the invention to provide a method and a composition for treating inflammatory skin conditions.

DETAILED DESCRIPTION OF THE PRESENT INVENTION

The objects of the present invention can be achieved by the administration of serine protease inhibitors alone or in combination in a suitable pharmaceutical form to patients suffering from non-bronchial inflammatory conditions which are associated with mast cell implicated diseases and which includes burns.

The present invention provides a pharmaceutical composition which comprises a compound of this invention and a pharmaceutically acceptable carrier. The compound may be used alone or in combination with other serine protease inhibitors to provide a broad spectrum of treatment.

In the treatment of burns, a 20% solution of a serine protease inhibitor such as $\alpha$ 1-antitrypsin, alone or in combination with other serine protease inhibitors, in sterile water or saline solution, may be sprayed on the patient or the burn area may be wrapped in wet bandages. A wound healing or skin growth factor may be included. The treatment provides immediate relief of pain. The patient may then be treated with the solution daily until the healing process is normal. Depending upon the severity of the burns, the patient may be further treated with other medications to prevent infection.

The following examples further illustrate the practice of this invention, but are not intended to be limiting thereof. It will be appreciated that the selection of actual amounts of specific serine protease inhibitors to be administered to any individual patient (human or animal) will fall within the discretion of the attending physician and will be prescribed in a manner commensurate with the appropriate dosages will depend on the stage of the disease and like factors uniquely within the purview of the attending physician.

EXAMPLE I

A topical cream was prepared as follows:
A. The following mixture was prepared:

| | |
|---|---|
| $\alpha$, -antitrypsin | 1.0 g |
| Olive oil | 5.0 g |
| Cetanol | 2.0 g |
| Stearic acid | 5.0 g |
| Glycerin aliphatic acid ester | 12.0 g |
| Tween 60 | 0.5 g |

B. The following mixture was also prepared:

| | |
|---|---|
| Propylene glycol | 0.5 g |
| Methyl paraben | 0.1 g |
| Propyl Paraben | 0.02 g |
| Purified water | to 100 g in total |

The mixture of parts A and B were blended together by conventional means to give a total of 100 g. of 100% by weight topical cream which could be utilized for treatment of acne, eczema, psoriasis, or other inflammatory dermatological conditions. If desired secretory leucocyte protease inhibitor and/or alpha 2-macroglobulin may be added in an amount of 1.0 g to part A.

EXAMPLE II

An olegenous anhyrous ointment was prepared with the following composition:

| Composition | % |
|---|---|
| $\alpha$, -antitrypsin | 1.0 |
| Soy phosphatide | 4.0 |
| Plastibase 50W | 94.975 |
| Butylated hydroxytoluene | 0.025 |
| | 100.00 |

If desired, in lieu of alpha 1-antitrypsin as the active principal, there may utilized the combination of alpha 1-antichymotrypsin and alpha 1-antitrypsin. Other non-aqueous lipid miscible carriers may also be utilized. However, it is understood that other serine protease inhibitors can also be similarly formulated.

EXAMPLE III 1000 mg of PROLASTIN, a composition sold by Cutter Biological, Miles Inc., comprising about 70% $\alpha'$-antitrypsin and about 10-18% $\alpha'$-antichymotrypsin was dissolved in 50 ml of saline solution. A patient suffering from atopic dermatitis with swelling and open lesions of the hand was treated by immersing the hand in the solution. Pain disappeared within 6-10 minutes of treatment. Treatment was continued for 1 hour. The redness and swelling disappeared after 1 hour. Twenty four hours after the treatment the lesions were healing without treatment with any other drugs.

A similar composition was utilized as an otic wash for dogs with ear infections followed by the administration of a steriod.

EXAMPLE IV

A suitable cream for topical use was prepared by admixing 43 g of PROLASTIN from Cutter Biological Laboratories, with 6 ml of water and 1000 g of a balm available under the trademark AQUAPHOR, sold by Beiesdorf Inc., Norwalk Conn. AQUAPHOR comprises a mixture of petrolatum, minerial oil, wax and wool wax alcohol.

The cream is useful for minor irritations and in the treatment of inflammatory skin conditions.

EXAMPLE V

In the treatment of colitis a 20% solution with PROLASTIN may be prepared and administered as an enema.

A similar result will be found with an secretory leucocyte protease inhibitor.

We claim:

1. A method for the treatment of non-bronchial mast cell implicated diseases or injury in mammals which comprises administering to the site of the disease or injury an effective amount of alpha 1-antitrypsin, its salt or derivative which has an affinity to mast cells and/or their mediators and T-cell mediators.

2. The method of claim 1 wherein said alpha 1-antitrypsin is recombinant.

3. The method of claim 1 wherein said mast cell implicated disease is dermatitis or psoriasis and said alpha 1-antitrypsin is administered topically.

4. The method of claim 1 wherein said disease is colitis.

5. The method of claim 1 wherein said mammal is an animal.

6. The method of claim 1 wherein said mammal is human.

7. The method of claim 1 wherein said mediators comprise neutrophils and eosinophils.

8. The method of claim 1 wherein said mediators comprise cathepsin G and elastase.

9. The method of claim 1 wherein said mediators comprise kinins.

10. The method of claim 1 wherein said mammal has an elevated IgE level.

11. The method of claim 1 wherein said disease is atopic dermatitis.

12. A method for inhibiting histamine release in a patient suffering from a mast cell implicated disease which comprises administering to said patient an effective amount of alpha 1-antitrypsin, its salts or derivatives which has an affinity to mast cells and/or their mediators and T-cells mediators.

* * * * *